US011083697B2

(12) United States Patent
Schmeichel et al.

(10) Patent No.: US 11,083,697 B2
(45) Date of Patent: *Aug. 10, 2021

(54) COMPOSITIONS AND METHODS USEFUL FOR TREATMENT OF RESPIRATORY ILLNESS

(71) Applicant: The Procter & Gamble Company, Cincinnati, OH (US)

(72) Inventors: Kelly Lee Schmeichel, Cincinnati, OH (US); Jayant Eknath Khanolkar, Singapore (SG); Douglas William Gledhill, St. Peters, MO (US); Susan Elaine Criss, Maineville, OH (US); Niranjan Ramji, Mason, OH (US); Elaine Rose Costeines, Maineville, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/109,835

(22) Filed: Aug. 23, 2018

(65) Prior Publication Data
US 2018/0360781 A1 Dec. 20, 2018

Related U.S. Application Data

(63) Continuation of application No. 16/011,700, filed on Jun. 19, 2018, which is a continuation of application No. 11/408,299, filed on Apr. 21, 2006, now Pat. No. 10,022,339.

(51) Int. Cl.
*A61K 31/137* (2006.01)
*A61K 31/473* (2006.01)
*A61K 31/485* (2006.01)
*A61K 31/495* (2006.01)
*A61K 31/519* (2006.01)
*A61K 31/522* (2006.01)
*A61K 31/55* (2006.01)
*A61K 31/616* (2006.01)
*A61K 45/06* (2006.01)

(52) U.S. Cl.
CPC .......... *A61K 31/137* (2013.01); *A61K 31/473* (2013.01); *A61K 31/485* (2013.01); *A61K 31/495* (2013.01); *A61K 31/519* (2013.01); *A61K 31/522* (2013.01); *A61K 31/55* (2013.01); *A61K 31/616* (2013.01); *A61K 45/06* (2013.01)

(58) Field of Classification Search
CPC .. A61K 31/137; A61K 31/473; A61K 31/485; A61K 31/495; A61K 31/519; A61K 31/522; A61K 31/55; A61K 31/616; A61K 45/06; A61P 11/00; A61P 11/02
See application file for complete search history.

(56) References Cited

U.S. PATENT DOCUMENTS

| | | | |
|---|---|---|---|
| 3,169,092 | A | 2/1965 | Petraglia et al. |
| 3,293,045 | A | 12/1966 | Griffin |
| 3,480,185 | A | 11/1969 | Steinberg |
| 3,710,795 | A | 1/1973 | Higuchi et al. |
| 4,049,803 | A | 9/1977 | Cotty et al. |
| 5,196,436 | A | 3/1993 | Smith |
| 5,296,209 | A | 3/1994 | Simone et al. |
| 5,480,674 | A | 1/1996 | Peterson |
| 5,660,833 | A | 8/1997 | Medenica |
| 5,759,579 | A | 6/1998 | Singh et al. |
| 6,028,222 | A | 2/2000 | Dietlin et al. |
| 6,187,340 | B1 | 2/2001 | Fukuta et al. |
| 6,218,428 | B1 | 4/2001 | Chynn |
| 6,287,597 | B1 | 9/2001 | Gordziel |
| 6,572,849 | B2 | 6/2003 | Shahinian, Jr. |
| 10,022,339 | B2 | 7/2018 | Martin et al. |
| 2002/0061340 | A1 | 5/2002 | Shahinian, Jr. |
| 2002/0082307 | A1 | 6/2002 | Dobrozsi et al. |
| 2003/0026826 | A1 | 2/2003 | Cherukuri et al. |
| 2003/0083354 | A1 | 5/2003 | Kiel et al. |
| 2003/0118654 | A1 | 6/2003 | Santos et al. |
| 2004/0029864 | A1 | 2/2004 | MacMillan |

(Continued)

FOREIGN PATENT DOCUMENTS

| | | |
|---|---|---|
| EP | 0306469 | 3/1989 |
| EP | 0387933 A1 | 9/1990 |

(Continued)

OTHER PUBLICATIONS

Wight Hat Ltd, Metric conversions. Milliters to US Teaspoons, Jul. 22, 2018, acccessed https://metric-conversions.org/volume/milliliters-to-us-teaspoons.htm (Year: 2018).*
"A Bevy of Bottles", PMPNews.com; Aug. 7, 1998—cited in EP opposition Oct. 28, 2014
International Search Report and Written Opinion dated May 27, 2009.
Anonymous: "Alka Seltzer Plus Cold & Cough Liquid", Internet, URL:HTTP://www.alkaseltzer.com/asp/products/colcough_liquid.html, 2007.
Anonymous: "New technologies unveiled by Magplastic at dring TEC-PET point 2005", Magplastic, Blow-Moulding Technology, Sep. 12, 2005; http://www.magplastic.com/PressReviews/2005%20-%20New%technologies.pdf.

(Continued)

*Primary Examiner* — Sarah Pihonak
(74) *Attorney, Agent, or Firm* — Jason J Camp; Amanda Herman Berghauer

(57) ABSTRACT

Disclosed are compositions including phenylephrine, its free and addition salt forms, and mixtures thereof, alone, or in combination with other pharmaceutical actives. The compositions have a pH of about 2 to about 5 and are substantially free of aldehydes. Also disclosed are methods of treating respiratory illness through administration of a composition comprising phenylephrine, its free and addition salt forms, and mixtures thereof alone, or in combination with other pharmaceutical actives, wherein the composition has a pH of from about 2 to about 5 and is substantially free of aldehydes.

27 Claims, No Drawings

(56) References Cited

U.S. PATENT DOCUMENTS

| | | | |
|---|---|---|---|
| 2004/0054012 A1 | 3/2004 | Dietlin et al. | |
| 2004/0162273 A1 | 8/2004 | Achong et al. | |
| 2004/0259952 A1 | 12/2004 | Abbas et al. | |
| 2004/0259955 A1* | 12/2004 | Umehara | A61K 31/135 514/649 |
| 2005/0214349 A1 | 9/2005 | Nie et al. | |
| 2005/0266031 A1 | 12/2005 | Dickerson et al. | |
| 2005/0266032 A1 | 12/2005 | Srinivasan et al. | |
| 2005/0267222 A1 | 12/2005 | Iwata et al. | |
| 2006/0039973 A1 | 2/2006 | Aldritt et al. | |
| 2006/0110476 A1 | 5/2006 | Haber et al. | |
| 2006/0121066 A1 | 6/2006 | Jaeger et al. | |
| 2006/0148837 A1 | 7/2006 | Giordano et al. | |
| 2006/0188450 A1 | 8/2006 | Clarot | |
| 2006/0216393 A1 | 9/2006 | Froseth et al. | |
| 2007/0024972 A1 | 2/2007 | Kuerz | |
| 2007/0098785 A1 | 5/2007 | Clarot et al. | |
| 2007/0178123 A1 | 8/2007 | Levenson et al. | |
| 2007/0179199 A1 | 8/2007 | Henning et al. | |
| 2007/0197661 A1 | 8/2007 | Bubnis et al. | |
| 2007/0249727 A1 | 10/2007 | Martin | |
| 2007/0254027 A1 | 11/2007 | Martin et al. | |
| 2008/0014274 A1 | 1/2008 | Bubnis et al. | |
| 2008/0069874 A1 | 3/2008 | Hall et al. | |
| 2010/0266699 A1 | 10/2010 | Buehler et al. | |
| 2011/0136851 A1 | 6/2011 | Jaeger et al. | |

FOREIGN PATENT DOCUMENTS

| | | |
|---|---|---|
| EP | 0473159 A1 | 3/1992 |
| EP | 1051155 B1 | 6/2002 |
| EP | 1559433 A1 | 8/2005 |
| EP | 1283043 B1 | 1/2008 |
| GB | 836747 | 6/1960 |
| GB | 895495 A | 5/1962 |
| GB | 1121358 A | 7/1968 |
| JP | S6333327 A | 2/1988 |
| JP | H0780760 A | 3/1995 |
| JP | 1995080760 | 8/1995 |
| JP | H09286723 A | 11/1997 |
| JP | H09286724 A | 11/1997 |
| JP | H09286726 A | 11/1997 |
| JP | H10167988 A | 6/1998 |
| JP | 2002212107 A | 7/2002 |
| JP | 2004217596 | 8/2004 |
| JP | 2004300138 A | 10/2004 |
| JP | 2005060294 A | 3/2005 |
| WO | WO9204559 A1 | 5/1992 |
| WO | WO9408551 | 4/1994 |
| WO | WO9614828 A1 | 5/1996 |
| WO | WO2003047502 A1 | 6/2003 |
| WO | WO2003059085 A1 | 7/2003 |
| WO | WO2004066978 A1 | 8/2004 |
| WO | WO2004084637 A1 | 10/2004 |
| WO | WO2005023236 | 3/2005 |
| WO | WO2006022996 A2 | 3/2006 |
| WO | WO2007098128 A1 | 8/2007 |
| WO | WO2007101115 | 9/2007 |
| WO | WO2007122581 A2 | 11/2007 |
| WO | WO2014120021 A1 | 8/2014 |

OTHER PUBLICATIONS

Chafetz, L. et al., "Phenolic Cyclization of Epinephrine, Metaproterenol, Metaraminol, Phenylephrine, and Terbutaline with Formaldehyde", Pharmaceutical Research, 1987, Plenum Publishing, vol. 4, No. 2, pp. 158-161.

Chi, Susan, "Oxidative degradation of Monoetahnolamine", Presentation at the First national Conference of Carbon Sequestration, Washington DC, May 14-14, 2001.

Covonia Cold & Flu Marketing Authorization dated Apr. 5, 2004—printed on Oct. 29, 2014.

Das Gupta et al., "Stability of Phenylephrine Hydrochloride nasal Drops", American Journal of Hospital Pharmacy, vol. 29, pp. 870-873, (1972).

Drug Label for Tylenol Cold Multi-Symptom Daytime—downloaded from www.drugcite.com Oct. 29, 2014.

El-Shibini, H.A.M., et al., "The stability of Phenylephrine, Part 1: The Rate of Degradation of the Amino Group".

Extract from Covonia website www.covonia.co.uk,com; printed Oct. 29, 2014.

Fenaroli's handbook of flavor ingredients, fifth ed. G. A. Burdock 2005, pp. 3-4, 221-222, 299-300, 671-672, 781-782, 1414-1415 and 1616-1617.

Fernandez, M.T. et al., "Iron and copper chelation by flavonoids: an electrospray mass spectrometry study", Journal of Inorganic Biochemistry, vol. 92, pp. 105-111 (2002).

Gupta, et al., "Chemical Stabilities of Lignocaine Hydrochloride and Phenylephrine Hydrochloride in Aqueous Solution", Journal of Clinical and Hospital Pharmacy, vol. 11, No. 6, pp. 449-452, (1986).

Li, Zhong et al., "Detection and quantification of low-molecular-weight aldehydes in pharmaceutical excipients by headspace gas chromatography", Journal of Chromatography A, 1104 (2006) 1-10.

Luduena, F.P., et al., "Effect of Ultra-Violet Irradiation of Phenylephrine Solutions," J. Pharm. Pharmacol., vol. 15, pp. 538-543, 1963.

Marin, A., et al., "Major Degradation Product identified in Several Pharmaceutical Formulations against the Common Cold", Analytical Chemistry. vol. 77, No. 2, pp. 471-477, Jan. 15, 2005.

Milliard, B.J., "The stability of aqueous solutions of phenylephrine at elevated temperatures: identification of the decomposition products", Journal of Pharm. Pharmacol., vol. 25, pp. 24P-31P, (1973).

Pharmaceutical and Medical Packaging (PMP, Jul. 1998).

Popenoe, D.D., "P&G Poster: Global Collaboration to Overcome Phenylephrine Degradation in Latin America OTC Products", 2002.

Public Assessment Report for PL 00240/0144; Published by Medicines and Healthcare Products Regulatory Agency, "Thornton and Ross Cold and Flu Formula Oral Solution", printed Oct. 29, 2014.

Reckitt Benckiser Lemship Document 12: Lemon Flavour Description, issued on Jan. 13, 2000.

Reckitt Benckiser Lemsip Aldehyde Content Summary dated Oct. 27, 2014; printed Oct. 30, 2014.

Reckitt Benckiser Lemsip Assembly Method dated Oct. 24, 2014; printed Oct. 30, 2014.

Reckitt Benckiser Lemsip Document 13: Lemon flavor description, issued on Apr. 20, 2016.

Reckitt Benckiser Lemsip Document 14: Certificate of analysis for batch No. 320613, Jul. 25, 2013.

Reckitt Benckiser Lemsip invoice dated Oct. 29, 2014; printed Oct. 30, 2014.

Reckitt Benckiser Lemsip Invoice to 3rd party, dated Apr. 6, 2004.

Reckitt Benckiser Lemsip Master Formulation Bill of Material dated Oct. 21, 2014; printed Oct. 30, 2014.

Reckitt Benckiser Lemsip Master Formulation Specification dated Oct. 21, 2014; printed Oct. 30, 2014.

Reckitt Benckiser Lemsip Packaging Pictures dated Oct. 29, 2014; printed Oct. 30, 2014.

Reckitt Benckiser Lemsip pH Summary dated Oct. 29, 2014; printed Oct. 30, 2014.

Reckitt Benckiser Lemsip Product Code dated Apr. 27, 2016.

Reckitt Benckiser Lemsip Sachets Packaging Record dated Mar. 24, 2004; printed Oct. 30, 2014.

Reckitt Benckiser Lemsip Total Aldehyde Content Summary—printed Oct. 30, 2014.

Reckitt Benckiser Lemsip Variation Application dated Oct. 1, 2001; printed Oct. 30, 2014.

Reckitt Benckiser Lemsip Variation Application Type II dated Oct. 4, 2001; printed Oct. 30, 2014.

Reckitt Benckiser Lemsip Variation Approval issued by the Medicines Control Agency dated Dec. 12, 2001; printed Oct. 30, 2014.

Remington (Science and Practice of Pharmacy), 19th ed., vol. 1, p. 806, 1995 p. 1-4.

Schou, S.A. et al., "Studies on the durability of Drugs—Manufacture and Stability of Metaoxedrine (Phenylephrine, Neo-Synephrine) Solution for Injection", Farm., vol. 25, pp. 350-357, (1951).

(56) References Cited

OTHER PUBLICATIONS

Summary of Product Characteristics for Covonia Cold and Flu—printed on Oct. 29, 2014.
Troup, A.E., "Degradation of Phenylephrine Hydrochloride in Tablet Formulations Containing Aspirin", Journal of Pharmaceutical Sciences, vol. 53, pp. 375-379, (1964).
United States Pharmacopeia 21st Review, National Formulary 16th Review, U.S. Pharmacopeial Convention, Rockville, MD, 1985, p. 828.
West, G.B., et al., "A note on the stability of solutions of Phenylephrine", Journal of Pharm Pharmacol., vol. 12, pp. 113-115, (1960).
Whittet, T.D. et al., "Factors Affecting Drug Stability", American Journal of Hospital Pharmacy, vol. 21, pp. 440-453, (1964).
All Office Actions for U.S. Appl. No. 11/657,860, filed Jan. 25, 2007.
All Office Actions for U.S. Appl. No. 15/251,337, filed Dec. 20, 2006.
All Office Actions for U.S. Appl. No. 16/128,579, filed Sep. 12, 2018.
All Office Actions for U.S. Appl. No. 11/408,299, filed Apr. 21, 2006.
All Office Actions for U.S. Appl. No. 16/011,700, filed Jun. 19, 2018.
All Office Actions for U.S. Appl. No. 16/109,823, filed Aug. 23, 2018.
All Office Actions for U.S. Appl. No. 16/109,827, filed Aug. 23, 2018.
All Office Actions for U.S. Appl. No. 16/109,830, filed Aug. 23, 2018.
All Office Actions for U.S. Appl. No. 11/413,766, filed Apr. 28, 2006.
U.S. Appl. No. 16/109,823, filed Aug. 23, 2018, Schmeichel et al.
U.S. Appl. No. 16/109,827, filed Aug. 23, 2018, Schmeichel et al.
U.S. Appl. No. 16/109,830, filed Aug. 23, 2018, Schmeichel et al.
All Office Actions, U.S. Appl. No. 15/930,540, dated Jan. 8, 2021.
Bindra et. al., Pharmaceutical Research, vol. 11, Issue No. 7, 1994, pp. 1060-1064.
Third Party Opposition filed for European Patent Application Ser. No. 07735601.2, dated Nov. 7, 2014, 19 pages.

* cited by examiner

COMPOSITIONS AND METHODS USEFUL FOR TREATMENT OF RESPIRATORY ILLNESS

FIELD OF THE INVENTION

The invention relates to liquid compositions useful for treatment of respiratory illness such as cold, flu, allergies, sinusitis, and rhinitis. More particularly, the invention relates to liquid compositions comprising phenylephrine, wherein the compositions have a defined pH and are substantially free of aldehydes.

BACKGROUND OF THE INVENTION

Respiratory illness encompasses a broad range of ailments, including viral infections such as cold and flu, as well as allergies, sinusitis, rhinitis, and the like. Respiratory illness may present as any of a variety of symptoms, such as runny nose, nasal or chest congestion, cough, sneezing, pressure, headache, aches, fever or sore throat. Pharmaceutical actives typically used to treat these symptoms generally fall into one of the following pharmaceutical classifications: antihistamines, decongestants, antitussives, expectorants, demulcents, anesthetics, analgesics, antipyretic and anti-inflammatory agents. The products for treating respiratory symptoms associated with respiratory illness are manufactured in a number of product forms, the most common being liquid syrups and elixirs for swallowing, mouth and throat drops and lozenges, tablets, caplets, capsules, and liquid-filled capsules and lozenges, effervescent tablets, and dry dissolvable powders, as well as inhalants and topical creams and lotions that release volatile agents that are inhaled through the nose into the respiratory tract. The oral compositions are typically swallowed immediately, or slowly dissolved in the mouth.

Products for relief of multiple symptoms may include various pharmaceutical actives such as pseudoephedrine, phenylephrine, and phenylpropanolamine (decongestants), guaifenesin (an expectorant), chlorpheniramine, diphenhydramine and doxylamine (antihistamines), dextromethorphan (cough suppressant), acetaminophen, ibuprofen, and aspirin (analgesics). Because these actives have different properties and stabilities, it is a challenge to formulate overall compositions containing actives wherein the actives are all stable and effective. In particular, the stability of certain pharmaceutical actives has been an on-going problem, especially when formulated in combination with other actives. Often, for example, liquid solutions discolor or one or more actives precipitates out of solution or is degraded. To illustrate, wherein phenylephrine is desired as a pharmaceutical active, one of the common problems associated with the formulation and use of phenylephrine is degradation. Phenylephrine may degrade in the presence of oxygen, aldehydes, certain acids including citric acid, and metals. The degradation of phenylephrine, even in solid dose forms, has also been reported.

Thus, there is an ongoing need for stable, effective compositions useful for the treatment of respiratory illness and associated symptoms.

SUMMARY OF THE INVENTION

The present invention is directed to compositions comprising phenylephrine. The compositions have a pH of from about 2 to about 5. The compositions are substantially free of aldehydes. The compositions can be in the form of, for example, liquids, elixirs, liquid-filled capsules, liquid-filled lozenges, dissolvable compositions, and inhalants, but are preferably orally administered liquid forms. The invention is further directed to methods of treating respiratory illness and symptoms thereof comprising orally administering a composition as described herein.

These and other aspects of the present invention are described in further detail herein.

DETAILED DESCRIPTION OF THE INVENTION

All weights, measurements and concentrations herein are measured at 25° C. on the composition in its entirety, unless otherwise specified.

Except where specific examples of actual measured values are presented, numerical values referred to herein should be considered to be qualified by the word "about".

Various documents including, for example, publications and patents, are recited throughout this disclosure. All such documents are hereby incorporated by reference.

All percentages and ratios are calculated by weight unless otherwise indicated. All percentages and ratios are calculated based on the total composition unless otherwise indicated.

Referenced herein may be trade names for components including various ingredients utilized in the present invention. The inventors herein do not intend to be limited by materials under a certain trade name. Equivalent materials (e.g., those obtained from a different source under a different name or reference number) to those referenced by trade name may be substituted and utilized in the descriptions herein.

In description of the invention, various embodiments or individual features are disclosed. As will be apparent to the ordinarily skilled practitioner, all combinations of such embodiments and features are possible and can result in preferred executions of the present invention.

While various embodiments and individual features of the present invention have been illustrated and described, various other changes and modifications can be made without departing from the spirit and scope of the invention. As will also be apparent, all combinations of the embodiments and features taught in the foregoing disclosure are possible and can result in preferred executions of the invention.

COMPOSITIONS OF THE PRESENT INVENTION

The present compositions are defined herein in a number of embodiments, all relating to the discoveries made by the present inventors. In particular, the inventors have discovered that the compositions of the present invention are made acceptably stable through formulation at a defined pH, and through formulation of the compositions such that the compositions are substantially free of aldehydes.

Phenylephrine

In one embodiment, the liquid compositions of the present invention comprise phenylephrine; its free and addition salt forms, and mixtures thereof, wherein the composition has a pH of from about 2 to about 5 and is substantially free of aldehydes. Illustrative salts of phenylephrine include phenylephrine hydrochloride and phenylephrine hydrobromide.

In one embodiment, the compositions of the present invention may comprise an amount of phenylephrine in the range of about 0.0001 mg to about 20 mg of phenylephrine, alternatively from about 0.01 to about 15 mg, and alternatively from about 5 mg to about 10 mg of phenylephrine, all per dose of the composition. By way of non-limiting example, an embodiment of the present invention may comprise about 10 mg of phenylephrine, per dose. Another embodiment of the present invention may comprise about 5 mg of phenylephrine, per dose.

In addition, in an embodiment of the present invention, the compositions of the present invention may comprise an amount of phenylephrine in the range of from about 0.0001% to about 1%, alternatively from about 0.001% to about 0.5%, and alternatively from about 0.01% to about 0.25%, all by weight of the composition.

Additional Pharmaceutical Actives

The compositions of the present invention can also comprise an additional pharmaceutical active. Pharmaceutical actives are readily known to the ordinarily skilled artisan and, as such, the actives are not bound by the descriptions provided herein. As illustrative examples, pharmaceutical actives may include, but are not limited to, antitussives, antihistamines, non-sedating antihistamines, decongestants, expectorants, analgesics, antipyretic anti-inflammatory agents, local anesthetics, anti-inflammatory agents, demulcents, and mixtures thereof.

By way of further illustration, specific additional pharmaceutical actives include but are not limited to dextromethorphan, acetaminophen, ephedrine, pseudoephedrine, phenylpropanolamine, ibuprofen, aspirin, ketoprofen, guaifenesin, ambroxyl, bromhexine, diphenhydramine, chlorpheniramine, doxylamine, triprolidine, clemastine, pyrilamine, promethazine, cetirizine, loratidine, oxycodone, hydrocodone, naproxen, brompheniramine, carbinoxamine, caffeine, benzonatate, pheniramine, fentanyl, azatedine, desloratadine, carbamazepine, buprenorphine, hydromorphone, indomethacin, oxymorphone, phenol, codeine, mesalamine, dichlophenac, sulindac, beclomethaxone, meloxicam, fenoproten, mometasone, menthol, benzocaine, dipyridamole, methscopolamine, the free and the addition salt forms thereof, and mixtures thereof.

In one embodiment specific additional pharmaceutical actives include but are not limited to dextromethorphan, acetaminophen, doxylamine, and guaifenesin.

In one embodiment, the compositions of the present invention may comprise an amount of additional pharmaceutical active in the range of about zero (0) mg to about 1,000 mg of each of at least one additional pharmaceutical active, alternatively from about 2.5 mg to about 750 mg, and alternatively from about 5 mg to about 650 mg of each of at least one additional pharmaceutical active, all per dose of the composition.

In one embodiment, the compositions of the present invention may comprise an amount of additional pharmaceutical active in the range of about 0% to about 15%, alternatively 0.0001% to about 10%, alternatively from about 0.001% to about 7%, and alternatively from about 0.01% to about 5%, all by weight of the composition.

pH

The present inventors have herein discovered that phenylephrine, present in the liquid compositions herein may achieve enhanced stability wherein the composition has a pH of from about 2 to about 5, alternatively from about 2 to about 4.75, further alternatively from about 2 to about 4.5, and further alternatively from about 3 to about 4.5.

These results could be explained, without being limited by theory, on the basis of the influence of pH on activation of the benzene nucleus by phenolic groups. In acidic medium, the phenolic group is undissociated whereas in alkaline medium it would exist as phenoxide ion.

Regardless of the actual mechanism(s), the present inventors find that low pH, as defined herein, assists greatly in the stabilization of phenylephrine. However it has also been noted by the inventors that certain pharmaceutical actives can react negatively with certain organic acids such as citric acid. Therefore, wherein certain buffers are used (e.g. citrate buffer), the buffer should be used in low levels, using only enough to achieve and maintain the desired pH.

As non-limiting examples, the present compositions may comprise one or more acidulants in order to reach, and maintain, the presently defined pH. Acidity can be adjusted to and maintained within the requisite range by known and conventional methods. Acidulant as used herein means a substance added to a composition to lower the pH of the composition. Organic as well as inorganic edible acids may be used to adjust the pH of the liquid compositions herein. The acids can be present in their undissociated form or, alternatively, as their respective salts, for example, potassium or sodium hydrogen phosphate, potassium or sodium dihydrogen phosphate salts. Illustrative acids are edible organic acids which include citric acid, malic acid, fumaric acid, adipic acid, phosphoric acid, gluconic acid, tartaric acid, ascorbic acid, acetic acid, or mixtures thereof.

Substantially Free of Aldehydes

The compositions of the present invention are substantially free of aldehydes. As used herein, substantially free of aldehydes means that the composition comprises less than about 0.1%, alternatively less than about 0.05%, alternatively less than about 0.01% of total aldehydes, (i.e. compounds containing at least one aldehydic moiety), all by weight of the composition. As the inventors have discovered, formulating the compositions of the present invention to be substantially free of aldehydes upon manufacture compensates for the potential for formation of some amount of aldehyde in the composition during storage conditions.

Aldehydes are compounds that are well known to the ordinarily skilled artisan. Flavors are well known for use in health products for improving consumer acceptance, and many such flavors are aldehydic in structure. For example, characterizing compounds for cherry flavors include benzaldehyde and p-tolyl aldehyde. However, the inventors have found that these same flavors also often cause degradation of the phenylephrine used herein.

The present inventors have found that substantial removal of the aldehydes, as defined herein, greatly stabilizes the resulting composition. However, given the desire to provide compositions that are aesthetically acceptable, the present invention further provides optional alternatives to typical flavors and aromas containing significant levels of aldehyde. Such alternatives are herein referenced as non-aldehydic aesthetic agents.

To illustrate, the inventors have discovered that typical flavors and aromas may be substituted with non-aldehydic aesthetic agents such as flavor components which are selected from the group consisting of esters, ketones and alcohols, and also sweeteners, and mixtures thereof, in order to formulate flavors that smell and taste like cherry or other desired flavors.

As further examples, the present compositions may comprise a non-aldehydic aesthetic agent such as an ester selected from the group consisting of ethyl butyrate, benzyl acetate, benzyl butyrate, allyl isovalerate, allyl caproate, ethyl-2-methyl butyrate, ethyl methyl phenyl glycidate, and mixtures thereof. Utilizing these fruity esters can readily generate flavors similar to cherry and berry flavors.

The body of the flavor may also be important to make it take on character and endure. The use of ketones such as ionones are useful for this purpose. To illustrate, oxanone (4-(p-hydroxyphenyl)-2-butanone, raspberry ketone) along with trace amounts of ionones can provide this body.

As a further example, compounds such as cis-3-hexenol and trans-2-hexenyl acetate may add to the flavor. Furaneol and maltol may add a candy-like nuance.

In addition, the compositions of the present invention may optionally comprise low-aldehyde juice concentrates as flavoring agents.

The compositions of the present invention may optionally contain from about 0.0001% to about 5%, alternatively from about 0.01% to about 2%, and alternatively from about 0.025% to about 1.5% of non-aldehydic aesthetic agents, all by weight of the composition.

OTHER OPTIONAL COMPONENTS OF THE PRESENT COMPOSITIONS

Any or all components typically associated with respiratory illness and symptom treatment products can be used as required or as optional components herein. For example, exemplary components are disclosed in U.S. Pat. No. 5,196,436.

Sweeteners

The present liquid compositions may optionally comprise a sugar and/or other sweetener to provide sweetness and taste masking of pharmaceutical active(s) as well as to provide some body and thickness. Sucrose, or table sugar, often in liquid form, may be used. However, sucrose can hydrolyze to its constituent sugars, namely glucose and fructose. Glucose is an aldehyde, and therefore may be less desirable for use herein. However, the present inventors discover herein that the effect of sugar on phenylephrine is less than that of traditional aldehyde-containing flavors and aromas. Nonetheless, improved stability can be achieved when low levels of sugar are used, in addition to inclusion of a non-aldehydic aesthetic agent if an aesthetic agent is used, such that the composition remains substantially free of aldehydes as described herein. Relatively highly pure grades of sugars, having undergone less hydrolysis to monosaccharides, may assist in lowering levels of aldehydes as well. High fructose corn syrup can also be used, though is less desirable because it contains aldehydes.

For example, the compositions of the present invention can contain sugar, such as sucrose, in a liquid solution in the range of from about 10% to about 70% sugar solution by weight of the composition, and alternatively from about 15% to about 60% sugar solution by weight of the composition, wherein the sugar solution can comprise from about 50% to about 70% sugar by weight of the sugar solution.

Alternatively, or additionally if greater sweetening is desired, sugar alcohols such as glycerin, sorbitol, maltitol, and mannitol can be used to provide sweetness and body.

If such sugar alcohol solutions are used, they can be used in a range of from about 0% to about 30% solution by weight of the composition, and alternatively from about 10% to about 25% solution by weight of the composition, wherein the sugar alcohol solution may comprise from about 60% to about 80% sugar alcohol by weight of the sugar alcohol solution. For example, a 70% by weight sugar alcohol solution can be used at 20% by weight of the composition, resulting in 14% sugar alcohol by weight of the composition.

Sweetness levels can also be supplemented with the use of an artificial sweetener. Non-limiting examples of artificial sweeteners are selected from sodium saccharine, acesulfame potassium, sucralose, aspartame, monoammonium glycyrrhizinate, neohesperidin dihydrochalcone, thaumatin, neotame, cyclamates, and mixtures thereof. Generally, such artificial sweeteners are solids when used in sweetening compositions such as those of the present invention.

Wherein an artificial sweetener is utilized in the present inventive compositions, the compositions may comprise from about 0.0001% to about 5% artificial sweetener, alternatively from about 0.0425% to about 3.5% artificial sweetener, and alternatively from about 0.05% to about 2.0% artificial sweetener, all by weight of the composition.

Solvents

The present liquid components typically comprise a solvent. In one embodiment, the solvent is water-soluble or water miscible. As used herein, solvent means a substance used to dissolve phenylephrine and/or other pharmaceutical active(s).

Non-limiting examples of solvents may be selected from water, propylene glycol, ethanol, glycerol, sorbitol, and mixtures thereof.

In one embodiment, the solvent is selected from water, propylene glycol, ethanol, and mixtures thereof. There are also mixtures of the solvents that may be useful for certain product forms of the present invention. For example, wherein the product form is an elixir, liquid-filled capsule or liquid-filled lozenge, the solvent may optionally be a mixture of propylene glycol, ethanol, and water.

The level of each solvent that makes up the mixture is dependent on the solubility of the active(s) and the aesthetic benefits sought by the formulator. For example, for the compositions of the present invention, the composition may optionally comprise from about 40% to about 95% total solvents, or from about 50% to about 90%, or from about 60% to about 85% total solvents, all by weight of the composition. The example ranges of total solvents given above do not include any solvent that may be present in a sugar solution, if a liquid sugar solution is used in the composition.

Metal Chelators

The present compositions may optionally comprise a metal chelator. It has been found that trace amounts of heavy metal ions may catalyze auto-oxidation reactions that may compromise stability of the final composition.

The compositions may therefore optionally include a chelating agent. Chelating agents are well known to the ordinarily skilled artisan. Non-limiting examples of chelating agents include but are not limited to the salts of disodium and calcium salts of ethylene diamine tetraacetic acid (EDTA), tetrasodium EDTA, sodium hexametaphosphate (SHMP), citric acid, phosporic acid, di(hydroxyethyl)glycine, 8-hydroxyquinoline, and mixtures thereof. Trivalent metal chelating agents such as galactomannans complexed with iron may also be useful.

Wherein the compositions herein comprise a chelaing agent, the compositions may optionally comprise from about 0.0001% to about 1% of the chelating agent, alternatively from about 0.001% to about 0.5%, and alternatively from about 0.01% to about 0.3% of the chelating agent, all by weight of the composition Reducing Agents The present compositions may also optionally comprise a reducing agent. The inclusion of a reducing agent may have a beneficial chemical stabilizing effect on the pharmaceutical actives used in the present invention. Therefore, the reducing agents useful in the composition depend on the active selected and its solubility.

As used herein, the reducing agent is a substance that has a lower redox potential than the pharmaceutical active or other adjuvant that it is intended to protect from oxidation.

Thus, reducing agents are more readily oxidized than the pharmaceutical active or other adjuvant and are effective in the presence of oxidizing agents.

Reducing agents have an "electrode potential value". The electrode potential value is defined by the Nernst equation and measured using standard electrochemical reference cells. The resulting values are therefore called the "Standard Electrode Potential", or $E°$, as measured in volts (V). Comparing Standard Electrode Potentials for different substances can be used to assess the effectiveness of different reducing agents.

The reducing agents useful in the present invention may optionally have $E°$ values greater than about $-0.119V$, and alternatively from about $-0.119V$ to $+0.250V$. Illustrative reducing agents are selected from the salts of metabisulfite and bisulfite, including their sodium and potassium salts, dithiothreitol, thiourea, sodium thiosulphate, thioglycolic acid, tert-butyl hydroquinone (TBHQ), acetyl cysteine, hydroquinone, salts thereof, and mixtures thereof.

Wherein a reducing agent is utilized, the present compositions may comprise from about 0.001% to 1%, alternatively from about 0.01% to about 0.5%, and alternatively from about 0.05% to about 0.1% of a reducing agent, all by weight of the composition.

Salts

The present compositions may optionally comprise a salt, such as a chloride salt, which has been further discovered to provide potential stability benefits. Non-limiting examples include sodium chloride, potassium chloride, ammonium chloride, and mixtures thereof.

Wherein the composition comprises a salt, the composition may optionally comprise from about 0.0001% to about 2%, alternatively from about 0.25% to about 1% of the salt, all by weight of the composition. Such salts may slow the dissociation of a pharmaceutical active from the hydrochloride salt of a pharmaceutical active. For example, having a chloride salt present slows the dissociation of phenylephrine from phenylephrine hydrochloride.

METHODS OF THE PRESENT INVENTION

In a further embodiment, the present invention is directed to methods of treating a respiratory illness comprising orally administering a composition as described herein to a mammal in need of such treatment. As used herein, the term "respiratory illness" encompasses a broad range of respiratory ailments, including viral infections such as influenza and common cold, as well as allergy, sinusitis, rhinitis, and the like. As further used herein, "treatment" with respect to respiratory illness means that administration of the referenced composition prevents, alleviates, ameliorates, inhibits, or mitigates one or more symptoms of the respiratory illness or the respiratory illness itself, or any like benefit with respect to the respiratory illness in a mammalian subject in need thereof, preferably in humans. As such, this includes, for example: preventing a respiratory illness or its associated symptoms from occurring in a mammal, for example when the mammal is predisposed to acquiring the respiratory illness, but has not yet been diagnosed with the illness; inhibiting the respiratory illness or its associated symptoms; and/or alleviating, reversing, or curing the respiratory illness or its associated symptoms. Insofar as the methods of the present invention are directed to preventing a respiratory illness, it is understood that the term "prevent" does not require that the respiratory illness be completely thwarted. Rather, as used herein, the term "preventing" or the like refers to the ability of the skilled artisan to identify susceptibility to respiratory illness (such as, for example, in humans during winter months), such that administration of the referenced compositions may occur prior to the onset of the symptoms associated with the illness.

Respiratory illness may present as any of a variety of symptoms, such as runny nose, nasal or chest congestion, cough, sneezing, pressure, headache, aches, fever, or sore throat. The mammal treated may be a human.

As used herein, the term "orally administering" with respect to the mammal means that the mammal ingests or is directed to ingest, or does ingest, one or more of the present compositions. Wherein the human is directed to ingest the composition, such direction may be that which instructs and/or informs the human that use of the composition may and/or will provide the relief from the respiratory illness (e.g. symptomatic relief, whether temporary or permanent) for example, relief from congestion. For example, such direction may be oral direction (e.g., through oral instruction from, or example, a physician, pharmacists, or other heath professional), radio or television media (i.e., advertisement), or written direction (e.g., through written direction from, for example a physician, pharmacist, or other health professional (e.g., scripts), sales professional or organization (e.g., through, for example, marketing brochures, pamphlets, or other instructive paraphernalia), written media (e.g., internet, electronic mail, or other computer-related media), and/or packaging associated with the composition (e.g., a label present on a container holding the composition). As used herein, "written" means through words, pictures, symbols, and/or other visible or tactile descriptors, such as Braille. Such information need not utilize the actual words used herein, for example, "respiratory", "illness", or "mammal", but rather use of words, pictures, symbols and the like conveying the same or similar meaning are contemplated within the scope of this invention.

Administration may be on an as-needed or as-desired basis, for example, once-monthly, once-weekly, or daily, including multiple times daily, for example, at least once daily, twice daily, three times daily, or four times daily or more.

The amount of composition administered may be dependent on a variety of factors, including the general quality of health of the mammal, type of mammal, age, gender, or severity of symptoms.

In one embodiment herein, the liquid oral composition is administered to the mammal in total dosage volumes, per dose, of from about 5 mL to about 50 mL of the liquid oral composition, alternatively of from about 10 mL to about 30 mL of the liquid oral composition.

EXAMPLES

The following examples further describe and demonstrate embodiments within the scope of the present invention. They are given for the purpose of illustration and are not to be construed as limitations of the present invention.

The compositions below may be made as follows. First, propylene glycol, alcohol and glycerin are added to a clean vessel. The optional additional pharmaceutical active(s), including, for example, acetaminophen, dextromethorphan, doxylamine, and flavor are added and stirred until dissolved. In a separate vessel, water is added to dissolve phenylephrine, color, buffering agents, sweeteners, and EDTA. The aqueous solution is added to the propylene glycol solution. The resulting solution is mixed with liquid sugar and additional water to bring (i.e. q.s.) volume to 100% and the composition is mixed until homogeneous.

Example 1

Below are illustrated various non-limiting examples of compositions of the present invention.

| Raw Materials | % w/w | % w/w | % w/w | % w/w | % w/w |
|---|---|---|---|---|---|
| Propylene Glycol | 40 | 40 | 20 | 10 | 30 |
| Doxylamine Succinate | 0.08 | 0.08 | 0.04 | 0.04 | 0.08 |
| Dextromethorphan HBr | 0.13 | 0.13 | 0.07 | 0.07 | 0.13 |
| Acetaminophen | 4.43 | 4.43 | 2.17 | 2.17 | 4.43 |
| Alcohol | 8.52 | 8.52 | 8.52 | 8.52 | 8.52 |
| Anethol (Flavoring Agent) | 0.01 | 0.01 | 0.01 | 0.01 | 0.01 |
| Glycerin | 10 | 10 | 10 | 10 | 10 |
| Purified Water | 5 | 5 | 3.505 | 9.94 | 5 |
| Green Shade | 0.005 | 0.005 | 0.005 | 0.005 | 0.005 |
| Sodium Citrate anhydrous | 0.17 | 0.17 | 0.17 | 0.17 | 0.17 |
| Citric Acid (Anhydrous) | 0.36 | 0.36 | 0.36 | 0.36 | 0.36 |
| Phenylephrine HCl | 0.07 | 0.07 | 0.03 | 0.03 | 0.07 |
| Sodium Saccharin | 0.07 | 0.07 | 0.07 | 0.07 | 0.07 |
| Liquid Sugar | 28.31 | 31.11 | 55 | 58.57 | 21.16 |
| Disodium EDTA | 1 | 0.05 | 0.05 | 0.05 | |
| Sorbitol Liquid 70% | | | | | 20 |
| Beta Carotene antioxidant | | | 2.00 | | |
| Water to 100% | QS | QS | QS | QS | QS |
| pH | 3.85 | 4.16 | 4.12 | 3.74 | 4.10 |

Propylene Glycol available from Dow Chemical Corp. Plaqremine, LA, USA
Doxylamine Succinate available from Honeywell Iropharm, Wicklow, Ireland
Dextromethorphan HBr available from Hoffman-LaRoche, Branchburg, NJ, USA
Acetaminophen available from Mallinckrodt, Raleigh, NC, USA
Alcohol (ethanol) available from Grain Processing Corp., Muscatine, IA, USA
Anethol available from IFF Dayton, NJ, USA
Glycerin available from the Procter & Gamble Company, Cincinnati, OH, USA
Green Shade available from Sensient Pharmaceuticals Tech, St. Louis, MO, USA
Sodium Citrate available from Hoffman-LaRoche, Branchburg, NJ, USA
Citric Acid available from ADM, Cork, Ireland
Phenylephrine HCL available from Iwaki, Ku Tokyo, Japan
Sodium Saccharin available from PMC Specialties Group, Inc., Cincinnati, OH, USA
Liquid Sugar available from Imperial Sugar, Port Wentworth, CA, USA
Disodium EDTA available from Akzo-Nobel, ZG Herkenbosch, The Netherlands
Sorbitol Liquid available from Roquette, Keokuk, IA USA
B Carotene available from Hoffman-LaRoche, Postfach, CH-4070, Basel, Switzerland Example 2

| RAW MATERIAL | w/w |
|---|---|
| Water | QS |
| Sodium Carboxymethylcellulose | 0.10 |
| Liquid Sugar | 17 |
| Phenylephrine HCl | 0.07 |
| Propylene Glycol | 40 |
| Sorbitol | 20 |
| Glycerin | 5 |
| Dextromethorphan HBr | 0.13 |
| Alcohol | 4.25 |
| Coolant | 0.02 |
| Flavor | 0.33 |
| Water | 5.27 |
| Sodium Benzoate | 0.1 |
| Citric Acid | 0.14 |
| Sodium Chloride | 0.50 |
| Sodium Saccharin | 0.09 |
| Coloring Agent | 0.003 |
| PH | 4.5 |

Sodium Carboxymethylcellulose available from Hercules, Hopewell, VA, USA
Liquid Sugar available from Imperial Sugar, Port Wentworth, CA, USA
Phenylephrine HCL available from Iwaki, Ku Tokyo, Japan
Propylene Glycol available from Dow Chemical, Plaquemine, LA, USA
Sorbitol available from Roquette, Keokuk, IA, USA
Glycerin available from the Procter & Gamble Company, Cincinnati, OH, USA
Dextromethorphan HBr available from Divis Hyderabad, India
Alcohol (ethanol) available from Grain Processing Corp., Muscatine, IA, USA
Coolant available from Takasago International Corp., Tokyo, Japan
Flavor available from IFF, Dayton, NJ, USA
Sodium Benzoate available from DSM, Rotterdam, the Netherlands
Citric Acid available from ADM, Cork, Ireland
Sodium Chloride available from Morton, Ritman, OH, USA
Sodium Saccharin available from PMC Specialties Group, Inc., Cincinnati, OH, USA
Coloring Agent available from Sensient Pharmaceuticals Tech, St. Louis, MO, USA The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A liquid composition comprising:
   (a) from about 0.01 mg to about 15 mg of a phenylephrine active, per dose of the liquid composition, selected from the group consisting of phenylephrine, its free and addition salt forms, and mixtures thereof;
   (b) a flavor which comprises one or more non-aldehydic aesthetic agents;
   (c) a sugar alcohol selected from the group consisting of glycerin, sorbitol, maltitol, mannitol, and mixtures thereof; and
   (d) a solvent selected from the group consisting of water, ethanol, propylene glycol, and mixtures thereof;
   wherein the liquid composition is a solution;
   wherein the liquid composition has a pH of from about 2 to about 5; wherein the liquid composition comprises a ratio of propylene glycol to sorbitol of about 0.5:1 to

5:1; and wherein the liquid composition comprises less than about 0.1% of total aldehydes, by weight of the liquid composition.

2. The liquid composition according to claim 1 wherein the phenylephrine active is phenylephrine hydrochloride.

3. The liquid composition according to claim 2 which comprises less than about 0.05% of total aldehydes, by weight of the liquid composition.

4. The liquid composition according to claim 3 which comprises from about 0.0001% to about 5% of total non-aldehydic aesthetic agents, by weight of the liquid composition.

5. The liquid composition according to claim 4 wherein at least one of the non-aldehydic aesthetic agents is an ester.

6. The liquid composition according to claim 4 wherein at least one of the non-aldehydic aesthetic agents is a ketone.

7. The liquid composition according to claim 4 wherein at least one of the non-aldehydic aesthetic agents is an alcohol.

8. The liquid composition according to claim 4 which comprises less than about 0.01% of total aldehydes, by weight of the liquid composition.

9. The liquid composition according to claim 8 comprising from about 10% to about 25% of total sugar alcohol solution, by weight of the liquid composition.

10. The liquid composition according to claim 9 comprising from about 60% to about 80% of total sugar alcohol, by weight of the sugar alcohol solution.

11. The liquid composition according to claim 1 further comprising an artificial sweetener selected from the group consisting of sodium saccharine, acesulfame potassium, sucralose, aspartame, monoammonium glycyrrhizinate, neohesperidin dihydrochalcone, thaumatin, neotame, cyclamates, and mixtures thereof.

12. The liquid composition according to claim 11 wherein the phenylephrine active is phenylephrine hydrochloride.

13. The liquid composition according to claim 12 which comprises less than about 0.05% of total aldehydes, by weight of the liquid composition.

14. The liquid composition according to claim 13 which comprises from about 0.0001% to about 5% of total non-aldehydic aesthetic agents, by weight of the liquid composition.

15. The liquid composition according to claim 14 wherein at least one of the non-aldehydic aesthetic agents is an ester.

16. The liquid composition according to claim 14 wherein at least one of the non-aldehydic aesthetic agents is a ketone.

17. The liquid composition according to claim 14 wherein at least one of the non-aldehydic aesthetic agents is an alcohol.

18. The liquid composition according to claim 14 which comprises less than about 0.01% of total aldehydes, by weight of the liquid composition.

19. The liquid composition according to claim 18 comprising from about 0.0001% to about 5% of total artificial sweetener, by weight of the liquid composition.

20. The liquid composition according to claim 19 comprising from about 0.0425% to about 3.5% of total artificial sweetener, by weight of the liquid composition.

21. The liquid composition according to claim 19 comprising from about 0.05% to about 2.0% of total artificial sweetener, by weight of the liquid composition.

22. The liquid composition according to claim 8 further comprising an artificial sweetener selected from the group consisting of sodium saccharine, acesulfame potassium, sucralose, aspartame, monoammonium glycyrrhizinate, neohesperidin dihydrochalcone, thaumatin, neotame, cyclamates, and mixtures thereof.

23. The liquid composition according to claim 22 further comprising a chelating agent.

24. The liquid composition according to claim 23 further comprising a reducing agent.

25. The liquid composition according to claim 23 wherein the chelating agent is selected from the group consisting of disodium and calcium salts of ethylene diamine tetraacetic acid (EDTA), terasodium EDTA, sodium hexametaphosphate (SHMP), citric acid, phosphoric acid, di(hydroxyethyl)glycine, 8-hydroxyquinoline, and mixtures thereof.

26. The liquid composition according to claim 24 wherein the chelating agent is disodium EDTA.

27. The liquid composition according to claim 1 wherein the liquid composition comprises a ratio of propylene glycol to glycerin of 1:1 to 3:1.

* * * * *